United States Patent [19]
Willmitzer et al.

[11] Patent Number: 5,917,127
[45] Date of Patent: Jun. 29, 1999

[54] PLASMIDS USEFUL FOR AND METHODS OF PREPARING TRANSGENIC PLANTS WITH MODIFICATIONS OF HABIT AND YIELD

[75] Inventors: Lothar Willmitzer; Uwe Sonnewald, both of Berlin; Antje Von Schaeven, Belau, all of Germany

[73] Assignee: Hoechst Schering AgrEvo GmbH, Berlin, Germany

[21] Appl. No.: 08/450,042

[22] Filed: May 25, 1995

Related U.S. Application Data

[63] Continuation-in-part of application No. 08/156,876, Nov. 23, 1993, Pat. No. 5,436,394, which is a continuation of application No. 07/653,689, Feb. 11, 1991, abandoned.

[30] Foreign Application Priority Data

Feb. 13, 1990 [DE] Germany ............................ 40 04 800

[51] Int. Cl.$^6$ .......................... C12N 15/29; C12N 15/82; A01H 5/00; A01H 4/00
[52] U.S. Cl. ...................... 800/298; 435/69.8; 435/201; 435/32.01; 435/468; 435/419
[58] Field of Search ................................ 800/205, 298; 435/69.8, 320.1, 201, 240.4, 172.3, 468, 419

[56] References Cited

U.S. PATENT DOCUMENTS 5,436,394   7/1995   Willmitzer et al. .................... 800/205

OTHER PUBLICATIONS

Wenzler et al. Sucrose–regulated expression of a chimeric potato tuber gene in leaves of Transgenic tobacco plants. Plant Moleclar Biology 13: 347–354, 1989.

Mignery et al. Isolation and sequence analysis of cDNAs for the major potato tuber protein, patatin. Nucleic Acids Research, vol. 12, No. 21, 1984.

Mignery et al. Molecular characterization of the patatin multigene family of potato, Gene 62 (1988) 27–44, 1988.

*Primary Examiner*—Douglas W. Robinson
*Assistant Examiner*—Thomas Haas
*Attorney, Agent, or Firm*—Frommer Lawrence & Haug LLP

[57] ABSTRACT

There is disclosed plasmids for the preparation of transgenic plants which are modified through the transfer and the expression of genes localized on the plasmids, that influence the sugar metabolism or the sugar partitioning within a plant. In addition, transgenic plants with modified sugar metabolism or sugar partitioning are described. The genes cause a modified distribution of assimilates in the transgenic plant which result in significant changes in plant habit, such as size, leaf shape, internode separation and root formation, as well as improvements in plant yield. Plasmids and methods are also described which enable foreign proteins to be directed into specific tissues or portions of transgenic plants, including vacuoles, leaves and sink organs.

38 Claims, 8 Drawing Sheets

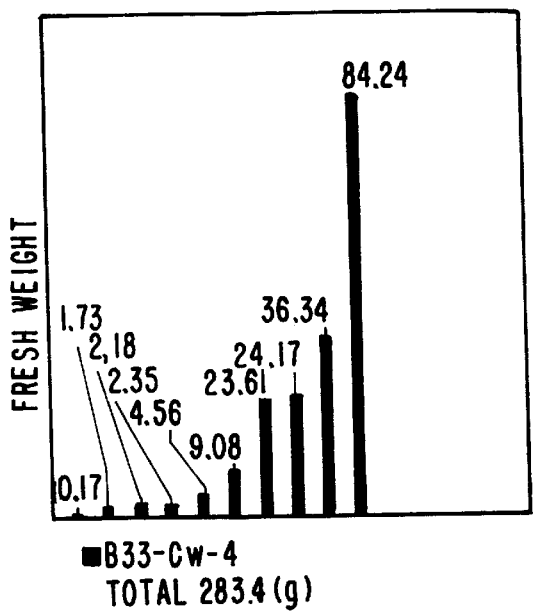
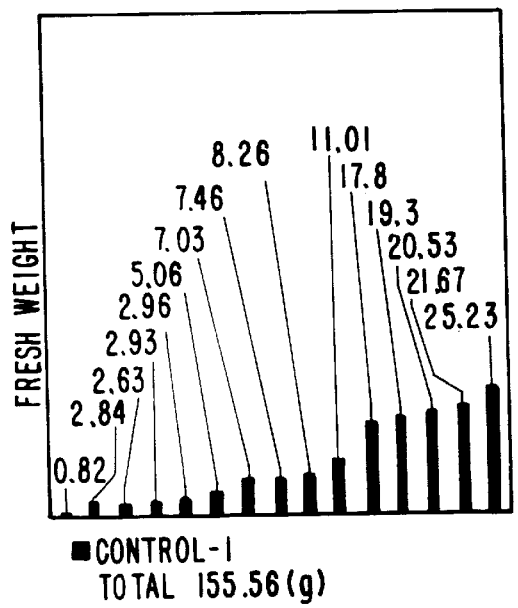
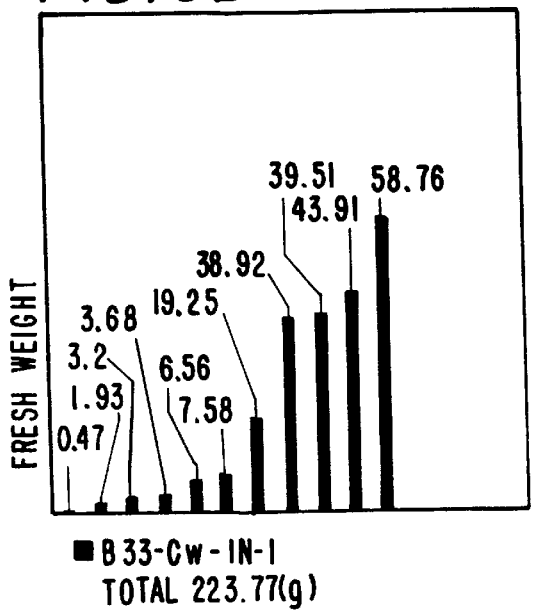
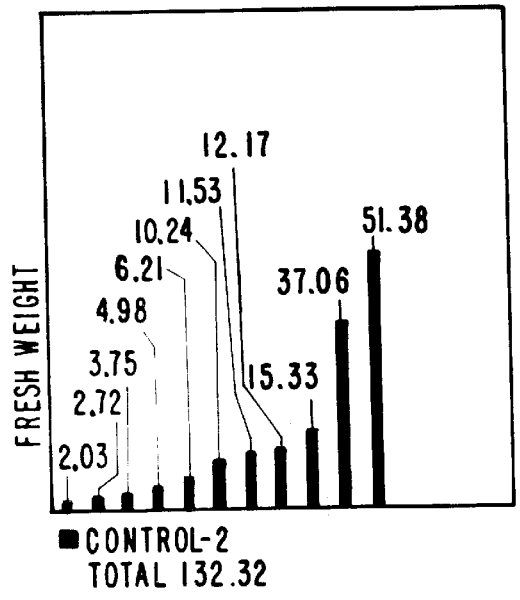

PLASMIDS USEFUL FOR AND METHODS OF PREPARING TRANSGENIC PLANTS WITH MODIFICATIONS OF HABIT AND YIELD

This is a continuation-in-part of application Ser. No. 08/156,876 filed Nov. 23, 1993 now U.S. Pat. No. 5,436,394 which was a continuation of application Ser. No. 07/653,689 filed Feb. 11, 1991, now abandoned.

BACKGROUND OF THE INVENTION

The present invention relates to new plasmids and methods for the preparation of transgenic plants, as well as the plants, that are modified through the transfer and the expression of genes which influence the sugar metabolism or the sugar partitioning within a plant, and which are localized on these plasmids.

The growth, the development and the yield of a crop or an ornamental plant depends on the energy that the plant gains through the fixing of $CO_2$ in carbohydrates during photosynthesis. The primary loci for photosynthesis are the leaves and to a lesser extent the stem tissue. The other organs of the plant, such as roots, seeds or tubers, do not make a material contribution to the formation of photoassimilates, but on the contrary are dependent for their growth on the supply of the photoassimilates from the photosynthetically active organs. This means that there is a flow in photosynthetically gained energy from photosynthetically active tissues to photosynthetically inactive parts of a plant.

The photosynthetically active tissues are generally known as sources. They are defined as net exporters of fixed carbon dioxide. The photosynthetically inactive parts of a plant are designated as sinks. They are defined as net importers of photosynthetically fixed carbon dioxide.

It is believed that the sinks have a strong influence in several ways, particularly in the efficient use of photosynthetic products as well as in their distribution within a plant. One example is the habit of the plant. Newly developing organs, such as very young leaves or other areas such as roots and seeds, are fully dependent on the photosynthesis performance of the sources. That means that the development of such organs is dependent on the distribution of the photoassimilates from sources within the plants. The influence on the formation of young leaves and also the formation of roots can have drastic effects on the habit of a plant, such as, for example, the size of a plant, the internode separation, the size and shape of a leaf, the appearance of a leaf and the number and shape of the roots. Further, the distribution of photoassimilates is quite critical to determining the yield of a plant.

Although the harvestable yield of a wheat plant has increased in the last decades, the total photosynthesis performance of wheat has not changed significantly. This can be explained by changes in the sink to source relationship, wherein the sinks which are important for the yield, such as seeds, take up essentially more photoassimilates than other parts of the plant which are unimportant as far as yield is concerned, such as the stem. In this case, through a shortening of the stem, a much more valid sink to source relationship in wheat could be achieved. This underlines the importance of the distribution of photoassimilates which are formed in the primary sources in higher plants in relation to both the habit and also the yield of plants.

It is not known which biochemical mechanism regulates the relationship of sink and source and the corresponding distribution of photoassimilates.

New biotechnological processes for the genetic change of dicotyledonous and monocotyledonous plants are known (Gasser and Fraley, 1989, Science 244, 1293–1299).

In most plants, photoassimilates are distributed within a plant in the form of sugars and preferentially in the form of sucrose. The distribution of sucrose between the source and sink tissues occurs by transport of sucrose via the phloem. One of the important determinants for the strength of a sink is the unloading of the phloem in the sink. In order to achieve a strong unloading of sucrose from the phloem into the sink, the sucrose should be transformed as soon as possible after leaving the phloem into a different chemical component that no longer has a chemical relationship to sucrose.

Changes of the plant habit can mean important improvements in known plants. For example, this can lead to a shortening of the stem to produce varieties which have greater wind resistance. A preferable distribution of the photoassimilates in harvestable organs such as seeds, e.g. of barley, wheat, soya beans or maize; leaves, for example tobacco; stems, for example sugar cane; tubers, for example potatoes; beets, for example animal feed beets and sugar beet; and fruit, for example tomatoes, lead to a higher yield of a plant. The redistribution of photoassimilates can also be performed in ornamental and garden plants, so as to produce plants with a completely new habit.

SUMMARY OF THE INVENTION

The object of the present invention is to provide plasmids and methods for the preparation of plants which are changed in their habit such as size, leaf shape, internode separation and root formation as well as in their harvestable yield. A further object of the invention is the provision of plants containing these plasmids.

It has now been found that plasmids, on which genes are located that influence the sugar metabolism or the sugar partitioning, after targeted introduction into the plants, are expressed in plants to produce transgenic plants. The expression of the genes leads to a changed distribution of photoassimilates in the transgenic plants. In this way, it has surprisingly been shown that the introduction of individual genes leads to significant modifications in the habit and yield of the plant.

Especially important changes in the habit and yield of plants, such as, for example, of potato and tobacco plants, can be achieved with plasmids that contain the DNA sequences of a gene of a sucrose modifying enzyme. The gene is preferably an invertase gene, such as for example, the invertase gene SUC2 from yeast. Furthermore, the sequences of this gene are fused to the regulatory regions of other genes which ensure the expression of the invertase gene in plant cells and plants.

The DNA sequence coding for the invertase gene can optionally be fused to a DNA sequence coding for a signal peptide which ensures translocation of a protein into the endoplasmic reticulum and then to the apoplast of a plant cell. Other signal peptides can be used which direct the protein to other locations within the plant cell or the plant. The regulatory regions are promoters and termination signals of plant genes.

Therefore the present invention relates to plasmids for the transformation of plant cells comprising the following DNA sequences i) a promoter active in plant cells, operably linked to ii) a DNA sequence encoding invertase, wherein the DNA sequence coding for an invertase may optionally be fused to a DNA sequence coding for a signal peptide that ensures translocation of the fusion protein to the apoplast in transformed plants.

Furthermore, the present invention relates to a process for the production of transgenic plants with increased yield in which a plasmid comprising the following DNA sequences
i) a promoter active in a plant cell, operably linked to
ii) a DNA sequence encoding invertase, is introduced into plant cells thereby producing transformed cells. Whole plants can be regenerated from the transformed plant cells. The DNA sequence coding for the invertase may optionally be fused to a DNA sequence coding for a signal peptide that ensures the translocation of the fusion protein to the apoplast in transformed plants.

In general, any promoter that is active in plant cells can be used. It is preferable to use promoters which lead to expression in typical storage organs such as seeds, fruits, tubers or beets. The promoters of the class I-patatin genes, such as the class I patatin gene B33 of *Solanum tuberosum*, have been reported to direct the expression of proteins in sink tissues, such as tomato fruit, potato tubers or sugar beets, and can be used in the present invention. Promoters leading to expression in seeds have also been described, for example the promoter of the USP gene of Vicia faba (Fiedler et al., 1993, Plant Mol. Biol. 22:669–679). Promoters which lead to expression in tomato fruit have been described in WO 9307257 and WO 9413797.

In order to direct the expressed protein to a specific compartment of the transformed plant cell, DNA sequences encoding signal peptides can be placed in front of the sequence coding for the desired protein. Preferably, the protein is invertase and it is preferred that the protein be expressed in the apoplast or vacuole of the transformed plant.

In order to direct the expressed protein to the apoplast, DNA sequences can be used that code for appropriate signal peptides. Signal peptides which ensure the direction of a foreign protein to the apoplast of a plant cell can be of bacterial or plant origin. Various such signal peptides have been described (for a review see Chrispeels, 1991, Ann. Rev. Plant Physiol. Plant Mol. Biol. 42:21–53).

Preferably, the DNA sequence coding for a signal peptide that directs the expressed protein to the apoplast is derived from a gene coding for the proteinase inhibitor II of *Solanum tuberosum*, preferably from the gene described in Keil et al. (1986, Nucl. Acids Res. 14:5641–5650). These sequences code for a signal peptide that leads to the translocation of the fusion protein into the endoplasmic reticulum of the cell and secretion into the apoplast when the sequences are fused in a frame with a coding region which codes for a protein.

The expression of an invertase in the apoplast of transgenic plants can modify the habit and yield across higher plant species, especially monocotyledonous or dicotyledonous plant species. Since the basic principles of sucrose metabolism are identical or highly similar in all higher plants, the effects which result from the expression of an invertase in the apoplast should be identical or similar in all higher plant species. The modification of plants through the expression of an invertase is especially interesting in crop plants, preferably in crop plants that produce harvestable storage organs, such as seeds, fruits, tubers or beets. Examples of such plants include corn, wheat, barley, maize, rice, potato, tomato and sugar beet.

Another preferred embodiment of the present invention relates to the direction of an invertase protein to the vacuole of transformed cells.

In order to direct the invertase to the vacuole of a transformed plant cell, the protein has to be provided with an appropriate signal sequence. Signal sequences which ensure the effective translocation of a fusion protein into a plant cell vacuole have not previously been described. The present invention provides DNA sequences which code for signal peptides that ensure the translocation of fusion proteins into the vacuole of plant cells. These sequences are derived from a gene coding for the patatin protein in *Solanum tuberosum*, especially from the gene pgT5 (Rosahl et al., 1986, Mol. Gen. Genet. 203:214–220). A suitable signal peptide which ensures effective translocation into the vacuole is coded by nucleotides +736 to +1400 of the pgT5 gene. This sequence is not only useful for directing an invertase protein to a plant cell vacuole but also for directing any desired endogenous or foreign protein to the vacuole of a plant cell.

Therefore, the present invention relates to DNA molecules for the transformation of plant cells, in which the DNA molecules comprise the following DNA sequences:
i) a promoter active in plant cells, operably linked to
ii) a DNA sequence coding for a signal peptide that ensures translocation of a protein to the vacuole of a plant cell,
iii) a DNA sequence coding for a protein in the same reading frame as the DNA sequence of ii), and
iv) a DNA sequence for the termination of transcription and the polyadenylation of the resulting transcript.

The DNA sequence coding for a signal peptide for vacuole targeting is preferably derived from a gene coding for a patatin protein, especially from the gene pgT5 of *Solanum tuberosum* (Rosahl et al., 1986, Mol. Gen. Genet. 203:214–220). Preferably this DNA sequence codes for the first 100 N-terminal amino acids, most preferably for the first 92 N-terminal amino acids of the immature protein coded by the pgT5 gene.

The present invention also relates to a method for providing a foreign protein or polypeptide in the vacuole of a plant cell. In this method, a DNA molecule, as described above, is introduced into plant cells which leads to the expression of a fusion protein that is translocated into the vacuole. As discussed above, the DNA sequence coding for the signal peptide is preferably derived from a gene coding for a patatin protein, especially from the gene pgT5 from *Solanum tuberosum*, and most preferably comprises nucleotides +707 to +1895 of this gene.

For the introduction of foreign genes into higher plants, a large number of cloning vectors are available which include a replication system in *E. coli* and a marker which allows for the selection of the transformed cells. The vectors include for example pBR 332, pUC series, M13 mp series, PACYC 184, etc. Using these systems, the sequence can be introduced into a suitable restriction position in the vector. The plasmid is then used for transformation in *E. coli*. The *E. coli* cells are cultivated in a suitable nutrient medium and then harvested and lysed. The plasmid is recovered. The plasmid can then be analyzed using any standard method of analysis including sequence analysis, restriction analysis, electrophoresis and other biochemical-molecular biological methods. After each manipulation, the DNA sequence which is used can be restricted and then joined to the next DNA sequence. The plasmid sequences can be cloned in the same or different plasmids.

Depending on the method used for introducing the desired gene into the plants, additional DNA sequences could be necessary. Should, for example the Ti- or Ri-plasmid be used for the transformation of the plant cells, at least the right border, and often both the right and the left borders of the Tiand Ri-plasmid T-DNA must be bound as a flanking area of the gene being introduced. The use of T-DNA for the transformation of plant cells has been intensively researched and is described in EP 120 516; Hoekema, The Binary Plant Vector System Offset-drukkerij Kanters BV, Alblasserdam, 1985, Chapter V; Fraley, et al., Crit. Rev. Plant Sci., 4: 1–46 and An et al., EMBO J. (1985) 4: 277–287.

Once the introduced DNA is first integrated in the genome, it is usually relatively stable and generally is not eliminated. The introduced DNA normally contains a selection marker which gives the transformed plant cells resistance against a biocide or an antibiotic, such as kanamycin, G 418, bleomycin, hygromycin or chloramphenicol, among others. The individually used marker should therefore allow for the selection of transformed cells as opposed to the untransformed cells which lack the introduced DNA.

A number of techniques are available for the introduction of DNA in a plant host cell. These techniques include transformation with T-DNA using *Agrobacterium tumefaciens* or *Agrobacterium rhizogenes* as the transformation media; fusion; injection or electroporation; as well as other possibilities. If Agrobacteria is used for the transformation, the DNA which is to be introduced is cloned in special plasmids, either in an intermediate vector or a binary vector. The intermediary vectors can be integrated based on sequences which are homologous to the sequences in the T-DNA, through homologous recombination in the Ti- or Ri-plasmids. These vectors also contain the Vir-region, necessary for the transfer of the T-DNA. Intermediary vectors cannot be replicated in Agrobacteria. However, by using a helper plasmid, the intermediary vector can be transferred to *Agrobacterium tumefaciens* (conjugation). Binary vectors can be replicated both in *E. coli* and in Agrobacteria. They contain a selection marker gene and a linker or polylinker, which are framed by the right and left T-DNA border regions. They can be transformed directly into the Agrobacteria (Holsters et al., Mol. Gen. Genet. (1978), 163: 181–187). The Agrobacteria serving as host cells should contain a plasmid that carries a Vir-region. The Vir-region is necessary for the transfer of the T-DNA into the plant cells. The plasmid can also contain additional T-DNA. The bacterium, so transformed, is used for the transformation of plant cells. For the transfer of DNA into the plant cells, plant explants can be cultivated in a suitable manner with *Agrobacterium tumefaciens* or *Agrobacterium rhizogenes*. From the infected plant material (for example leaf pieces, stem segments, roots and also protoplasts or suspension cultured cells), whole plants can be regenerated. The plants are grown in a suitable medium which can contain antibiotics or biocides which are used for selection. The plants can then be tested for the presence of the introduced DNA. Injection and electroporation do not require any special conditions for the plasmids. Simple plasmids, for example pUC derivatives, can be used.

The transformed cells grow within the plant in the usual way. The plants can be grown normally and crossed with plants which possess the same transformed genes or other genes. The hybrid plants which result from the cross will have the corresponding phenotypic properties.

Expressions and Abbreviations

Abbreviations:

bp, Kb=Base pairs, kilobases
d, kd=dalton, kilodalton
SDS=sodium dodecyl sulphate
tris=tris(2-aminoethyl)amine Expressions Class I Patatin Protein=A member of the patatin protein family which lacks a 22 bp sequence in the 5' untranslated region. (Mignery et al., 1988, Gene: 62, 27–44)
Class II Patatin Protein=A member of the patatin protein family which contains a 22 bp sequence in the 5' untranslated region. (Mignery et al., 1988, Gene: 62, 27–44)
Clone=Cell population that is derived from one of its own mother cells. Descendants are genotypically the same. By cloning, the homogeneity of cell lines can be increased further.
Electrophoresis=A biochemical separation process for separating nucleic acids from proteins according to size and charge.
Endoplasmic reticulum=intercellular membrane channels which serve for transporting of chemical and biochemical substances.
Expression=Activity of a gene.
Gene=Genetic factor; a unit of inheritance, carrier of part information for a particular specified characteristic. Genes consist of nucleic acids (eg. DNA, RNA).
Genome=Totality of the gene localized in the chromosomes of the cell.
Internodes=Shoot segments which are separated from one another through nodes (for example stems). The leaves are on the nodes.
Internode distance=The distance of various shoot segments from the nodes.
Klenow fragment=Fragment of DNA polymerase I of a size 76,000 d obtained by splitting with subtilisin. Possesses 5'-3' polymerase and 3'-5' exonuclease activity but not the 5'-3' exonuclease activity of the holoenzyme.
Ligation=Enzymatic formation of a phosphodiester bond between 5'-phosphate groups and 3'-hydroxy groups of the DNA.
Linker, Polylinker=Synthetic DNA sequence that contains one or more (polylinker) restriction cutting regions in direct sequence.
Northern blots,=Transfer and fixing of
Southern blots electrophoretically separate RNA or DNA on a nitrocellulose or nylon membrane.
Patatin=Trivial name for main storage protein of potato tubers; a glycoprotein of approximately 40 kd molecular weight.
Phenotype=A sum of characteristics which are expressed in an organism as opposed to its genotype.
Phloem=Sieve element of the vascular bundle of a plant through which water flows with dissolved substances.
Promoter=Control sequence of the DNA expression which realizes the transcription of homologous or heterologous DNA gene sequences.
Replication=Doubling of the DNA sequence.
Restriction enzymes=Restriction endonucleases which are a sub-group of the endodeoxyribonuclease class (for example EcoRI (specificity G↓AATTC and EcoRII↓CC ($^A_T$)GG, from *E.coli*) exhibit a high substrate specificity (↓=splitting position).
Restriction positions=A splitting position which is produced specifically by restriction enzymes.
Termination=Last stage of the protein synthesis, in which the polypeptide chain is completed.
Transformation=Introduction of exogenous DNA of a bacterial species into a receiver cell.
Transcription=Overwriting on an RNA of the genetic information contained in the DNA.
Vectors=Host specific replicatable structures, that take up genes and carry these into other cells. Plasmids can also be used as vectors.

The following plasmids were deposited under the terms and conditions of the Budapest Treatyat at the German Collection for Microorganisms (DSM) in Braunschweig, Germany, a recognized depository of the Budapest Treaty (deposit number):

On Feb. 12, 1990
  Plasmid p35S-Cy-INV (DSM 5785)
  Plasmid p35S-CW-INV (DSM 5788)
  Plasmid p33-CW-INV (DSM 5787)
  Plasmid p1700-CW-INV (DSM 5789)
  Plasmid p33-Cy-INV (DSM 5786)
On Aug. 20, 1990
  Plasmid p35S-V-INV (DSM 6142)
On Oct. 20, 1994
  Plasmid pBinAR-Hyg (DSM 9505)

A=Fragment A (529 bp); contains the 35S promoter of the cauliflower mosaic virus (CaMv). It contains a fragment which includes nucleotides 6909 and 7437 of the CAMV.
B=Fragment B (1726 bp); contains 23 nucleotides of a proteinase inhibitor II gene of a potato (nucleotides 923–945), which are fused via a linker of 7 base pairs to the suc gene from yeast, including nucleotides +64 to +1765.
C=Fragment C (192 bp); contains the polyadenylating signal of the gene 3 of the T-DNA of the Ti-plasmid pTiACH5.

The cutting positions are described in the following Example 1.

Figure 2:
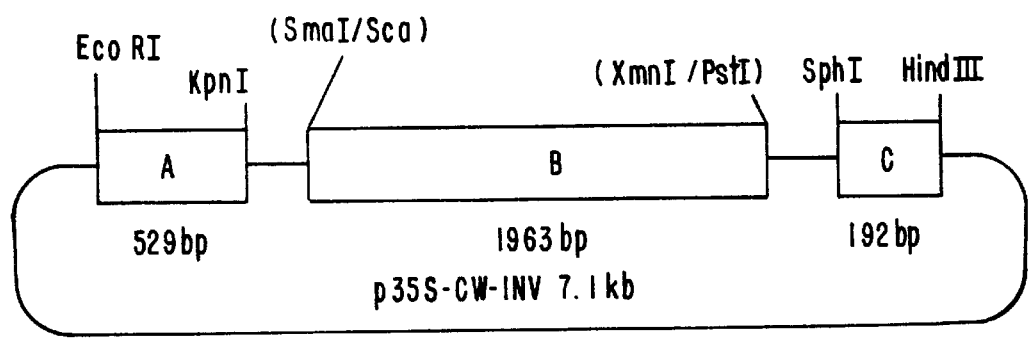

FIG. 2 shows the structure of the 7.1 kb size plasmid p35S-CW-INV. The plasmid contains the following fragments:

A=Fragment A (529 bp); contains the 35S promoter of the cauliflower mosaic virus (CaMV). It contains a fragment which includes nucleotides 6909 and 7437 of the CaMV.
B=Fragment B (1963 bp); contains the 923–1159 of a proteinase inhibitor II gene from potato, which are fused via a linker to the suc2 gene from yeast, including nucleotides +64 to +1765.
C=Fragment C (192 bp): contains the polyadenylating signal of the gene 3 of the T-DNA of the Ti-plasmid pTiACH5.

The cutting positions are described in the following Example 2.

Figure 3:
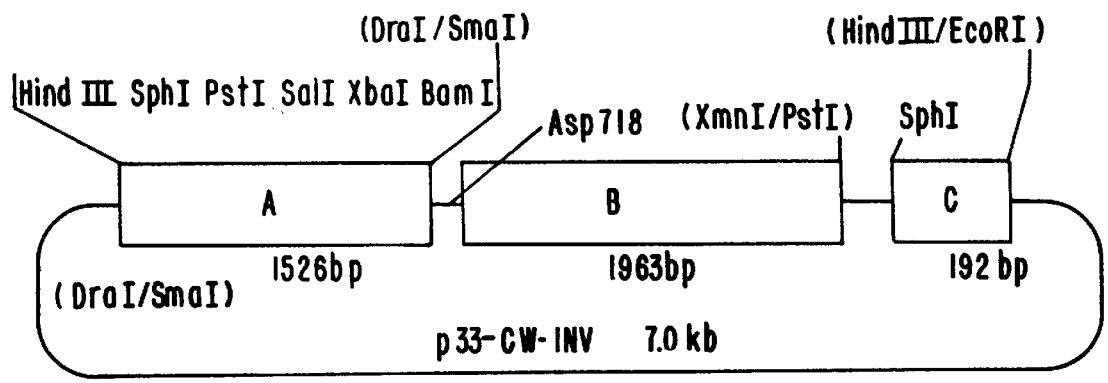

FIG. 3 shows the structure of the 7.0 kb size plasmid p33-CW-INV. The plasmid contains the following fragments:

A=Fragment A (1526 bp): contains the DraI-DraI fragment (position −1512 to position +14) of the promoter region of the patatin gene B33.
B & C=Fragment B (1963 bp) and C (192 bp). These fragments correspond to fragments B & C in plasmid p35S-CW-INV (FIG. 2).

The cutting positions are described in the following Example 3.

Figure 4:
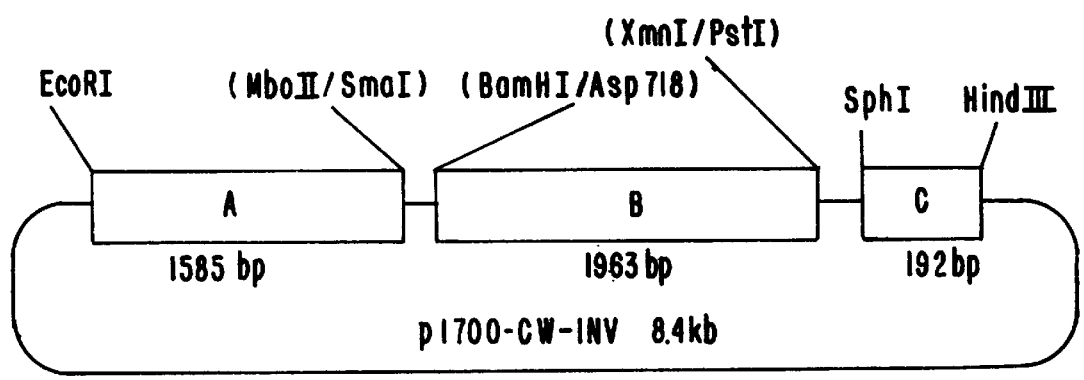

FIG. 4 shows the structure of the 8.4 kb size plasmid p1700-CW-INV. The plasmid contains the following fragments:

A=Fragment A (1585 bp): contains the EcoRI-MboII fragment of the ST-LS1-gene from potato.
B & C=Fragment B (1963 bp) and C (192 bp): correspond to the fragments B & C in plasmid p35S-CW-INV (FIG. 2).

The cutting positions are described in the following Example 4.

Figure 1:
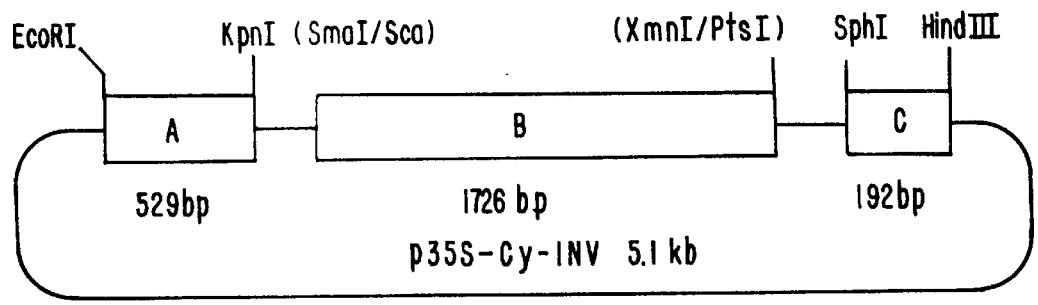
FIG. 1 shows the structure of the 5.1 kb size plasmid p35S-Cy-INV. The plasmid is made up from the following fragments.
Figure 5:
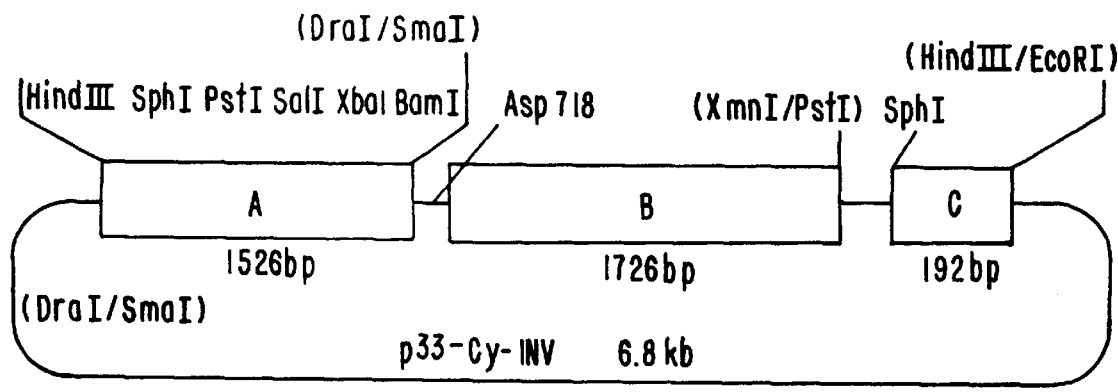

FIG. 5 shows the structure of the 6.8 kb size plasmid p33-Cy-INV. The plasmid contains the following fragments:

A=Fragment A (1526 bp): contains the DraI-DraI fragment (position −1512 to position +14) of the promoter region of the patatin gene B33.
B & C=Fragments B (1726 bp) and C (192 bp): correspond to fragments B & C in plasmid p35S-Cy-INV (FIG. 1).

The cutting positions are described in the following Example 5.

Figure 6:
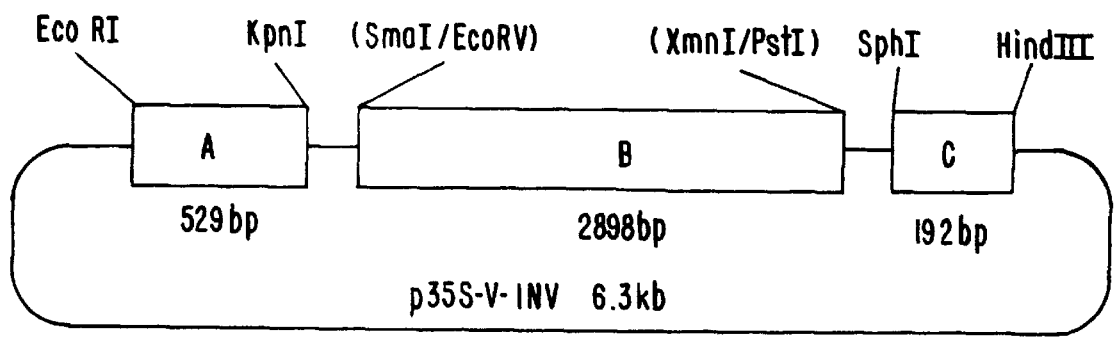

FIG. 6 shows the structure of the 6.3 kb size plasmid p35S-V-INV. The plasmid contains the following fragments:

A=Fragment A (529 bp): contains the 35S promoter of the cauliflower mosaic virus (CaMV).
B=Fragment B (2898 bp): contains nucleotides +707 to +1895 of the sequence of the genomic patatin clone pgT5, a linker of the sequence AGCTTTC and the SUC2 gene from yeast (nucleotides +64 to +1765).
C=Fragment C (192 bp): contains the polyadenylating signal of the gene 3 of the T-DNA of the Ti-plasmid pTiACH5 (nucleotides 11749–11939).

The cutting positions are described in the following Example 6.

Figure 7:
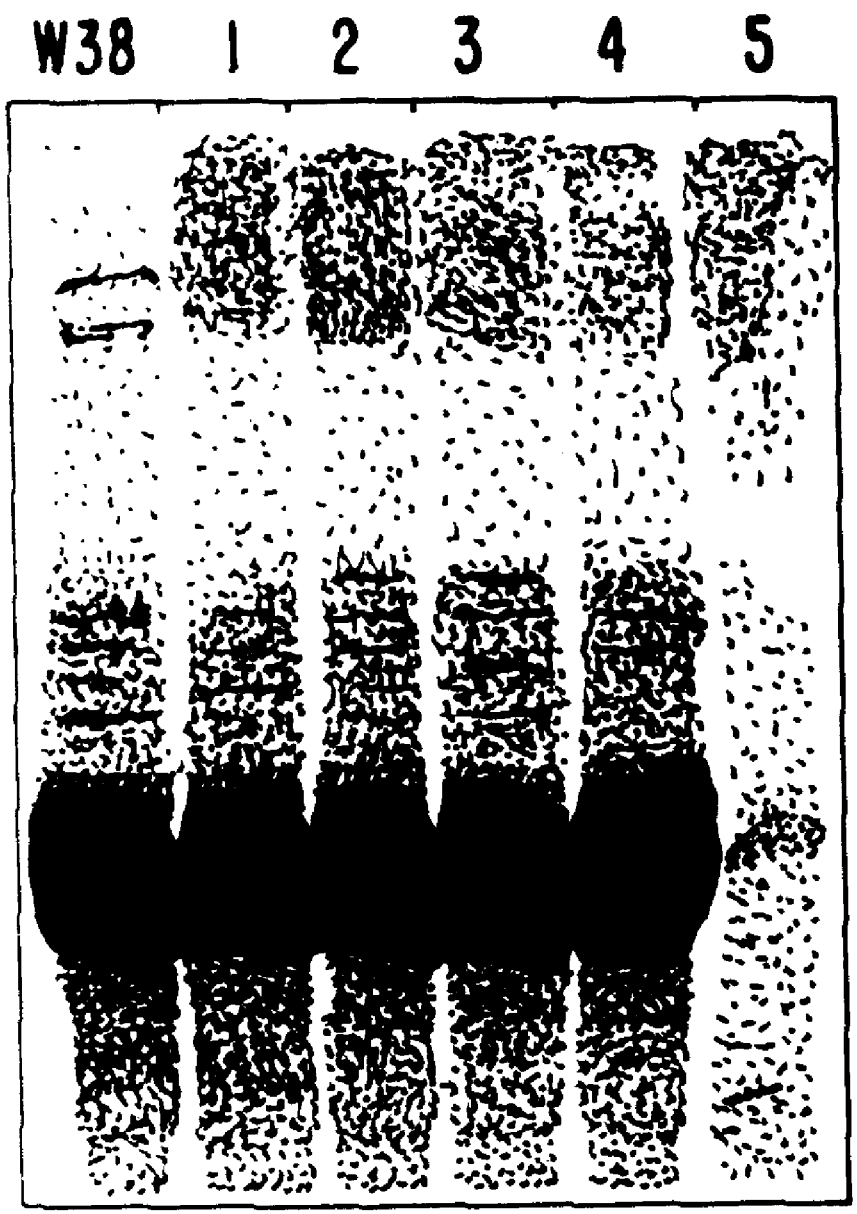

FIG. 7 shows the gel which provides in situ evidence of the invertase activity in leaf extracts from 5 independent transgenic tobacco plants (traces 1–5) as well as the absence of such activity in non-transformed plants (trace W38).

A=Gel area which contains reducing sugar. The black staining in traces 1–5 shows the presence of reducing sugar (invertase activity) in comparison with the control (trace W38).
B=The gel area of the protein fraction.

FIG. 8 shows the number, the size distribution (fresh weight) and the total fresh weight of the tubers of two potato plants, transformed with the plasmid p33-CW-INV (left side, plants B33-Cw-IN-4 and B33-CW-IN-1), as well as two control plants grown under the exact same conditions but not transformed (right side, plants control 1 and control 2). Each vertical column represents a tuber, whose weight in grams is given above the column. The total weight is also given in grams.

Figure 9:
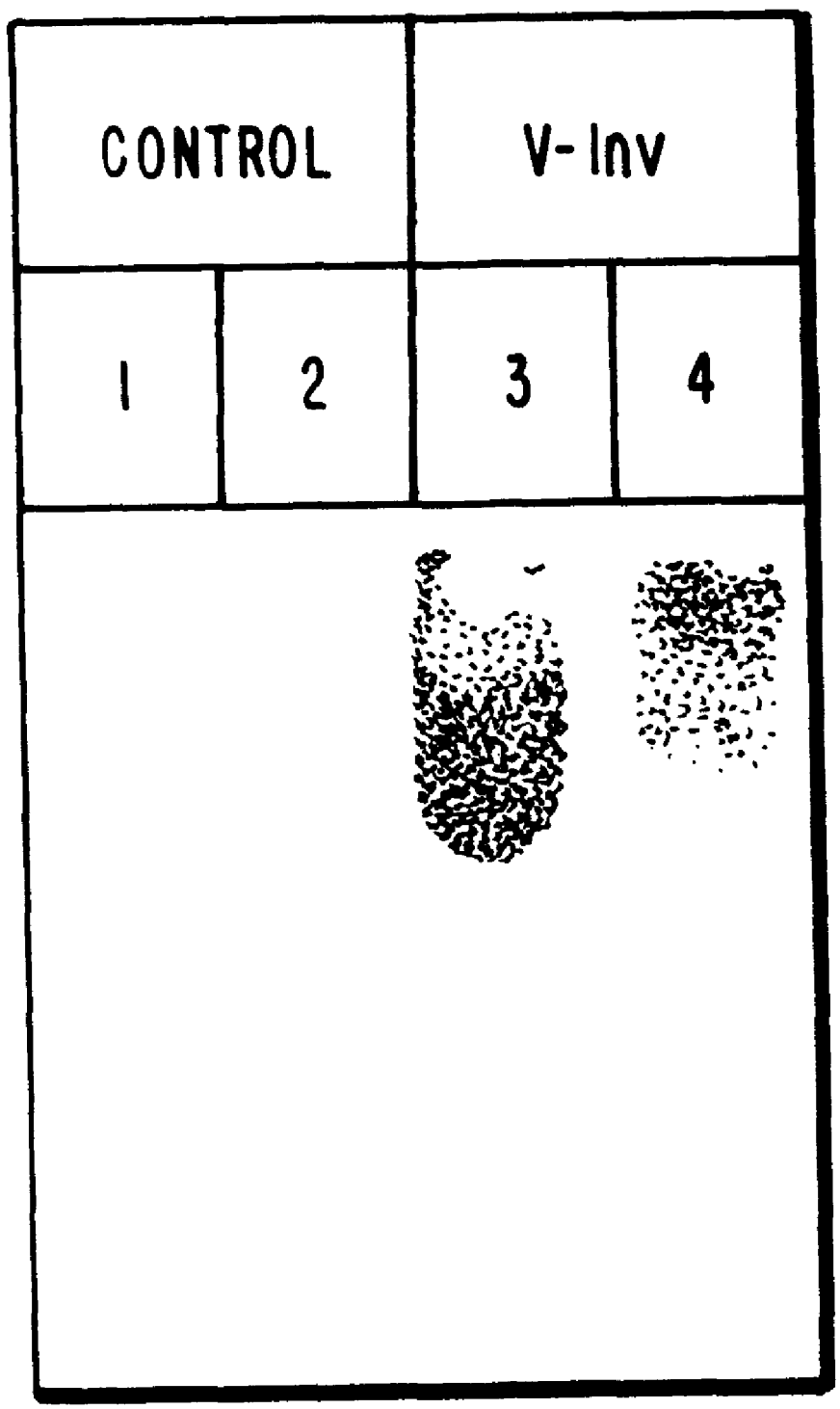

FIG. 9 shows the gel which provides in situ evidence of the invertase activity coded in the vacuoles of the tobacco plants transformed with the plasmid p35S-V-INV.
  Trace 1: protoplasts of untransformed tobacco plants;
  Trace 2: vacuoles of untransformed tobacco plants;
  Trace 3: protoplasts of transgenic tobacco plants;
  Trace 4: vacuoles of transgenic tobacco plants.

In each trace, comparable amounts of protoplasts and/or vacuoles which were normalized via the a-mannosidase activity, were applied. The black staining in traces 3 and 4 shows the invertase activity through the formation of reducing sugar. The intensity in both traces is similarly high which shows the exclusive localization of the invertase in the vacuoles. The invertase activity is not found in the protoplast and vacuoles of non-transformed tobacco plants (traces 1 and 2).

Figure 10:
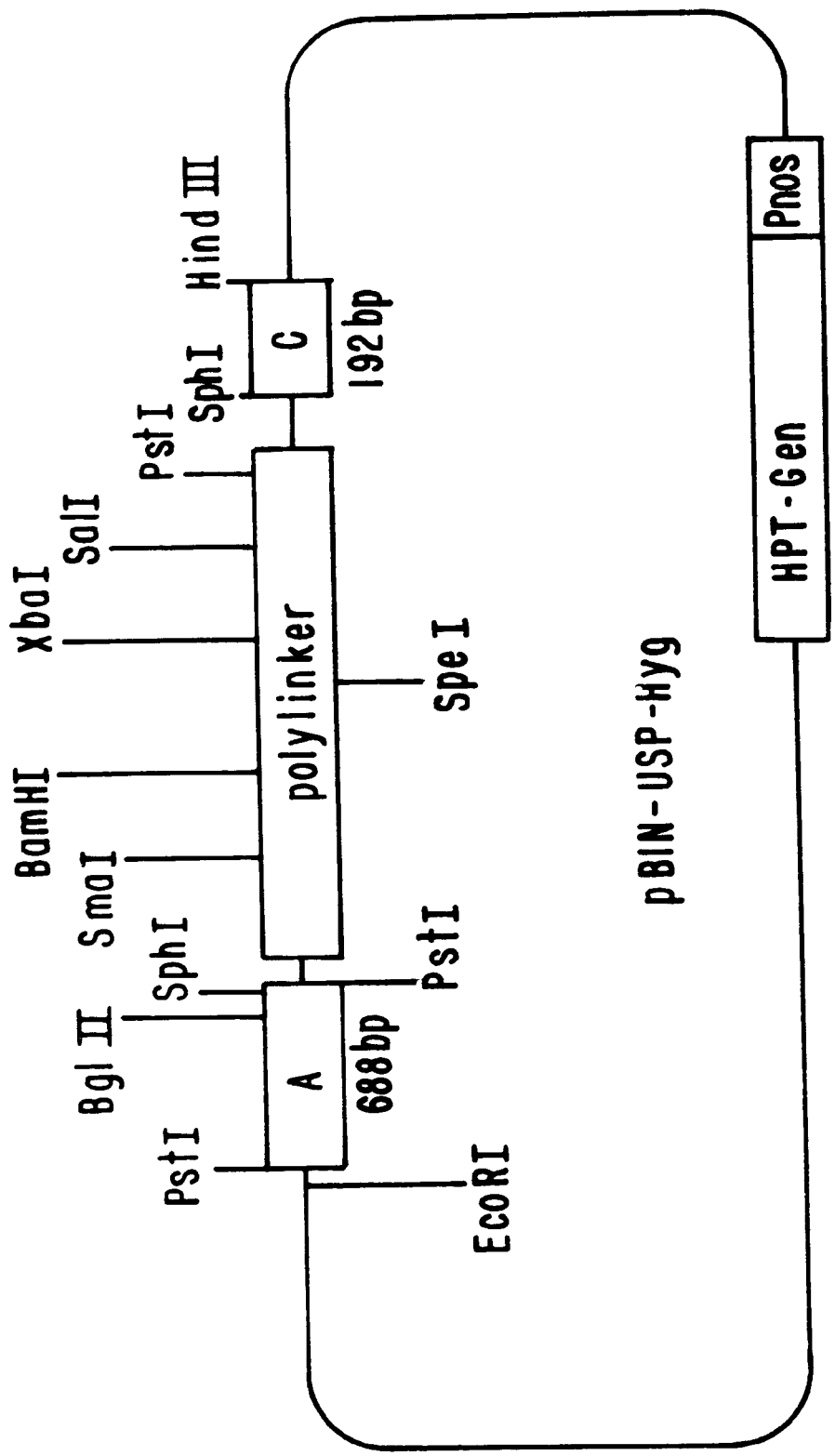

FIG. 10 shows the plasmid pBIN-USP-Hyg. The plasmid contains the following fragments:

A=Fragment A (688 bp); contains the promoter and the 5' nontranslated leader sequence of the USP gene of *Vicia faber*. It comprises a fragment which includes nucleotides −637 to +51 of the USP gene (Bäumlein et al., 1991, Mol. Gen. Genet. 225:459–467).

polylinker=polylinker with restriction sites for SmaI, BamHI, XbaI, SalI and PstI C=Fragment C (192 bp); contains the polyadenylation site of the gene 3 of the T-DNA of the Ti-plasmid pTiACH5.

Figure 11:
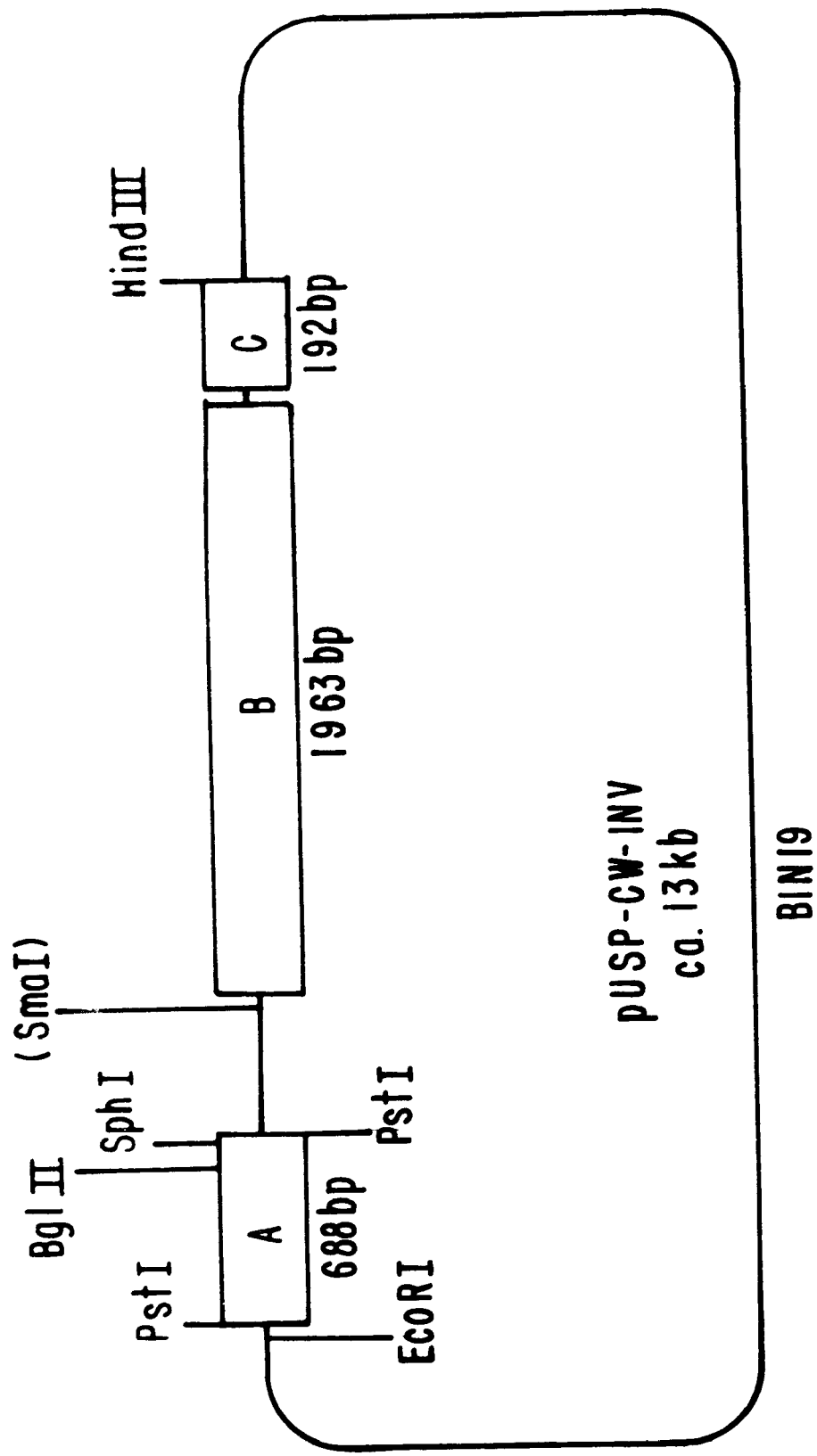

FIG. 11 shows the plasmid pUSP-CW-INV. The plasmid contains the following fragments:

A=Fragment A (688 bp); contains the promoter and the 5' nontranslated leader sequence of the USP gene of *Vicia faber*. It comprises a fragment which includes nucleotides −637 to +51 of the USP gene (Bäumlein et al., 1991, Mol. Gen. Genet. 225:459–467).

B=Fragment B (1963 bp); contains nucleotides +923 to +1159 of a proteinase inhibitor II gene of *Solanum tuberosum* (Keil et al., 1986, Nucl. Acids Res. 14:5641–5650) fused to the SUC2 gene of yeast (nucleotides +64 to 1765; Taussig and Carlson, 1983, Nucl. Acids Res. 11:1943–1954) via a linker sequence with the sequence ACC GAA TTG GGG ATC CCA GCT TTC (SEQ ID No. 1).

C=Fragment C (192 bp); contains the polyadenylation site of the gene 3 of the T-DNA of the Ti-plasmid pTiACH5.

The plasmid pUSP-CW-INV has a length of approximately 13 kb.

DESCRIPTION OF THE PREFERRED EMBODIMENTS

For a better understanding of this invention the following examples are given. Explanation of these experiments is given as follows:

1. Cloning Vectors

For cloning, the vectors pUC18/19 and pUC118 (Yanisch-Perron et al., Gene (1985), 33, 103–119) and pMPK110 (Eckes, Dissertation, University of Cologne (1984)) were used.

For the plant transformation, the gene structures were cloned in the binary vectors BIN19 (Bevan, Nucl. Acids Res. (1984), 12, 8711–8720).

2. Bacterial Species

For the pUC and M13 vectors, the *E. coli* strains BMH71-18 (Messing et al., Proc. Nat. Acad. Sci. USA (1977), 24, 6342–6346) or TB1 were used. For the vectors pMPK110 and BIN19, the *E. coli* strains TB1 was exclusively used. TB1 is a recombinant-negative, tetracycline resistant derivative of the species JM101 (Yanisch-Perron et al., Gene (1985), 33, 103–119). The genotype of the TB1 species is (Bart Barrel, personal communication): F' (traD36, proAB, lacI, lacZΔM15), Δ(lac, pro), SupE, thiS, recA, Sr1::Tn10 (Tc$^R$).

The plant transformation was carried out using *Agrobacterium tumefaciens* species LBA4404 (Bevan, M., Nucl. Acids Res. 12, 8711–8721, (1984); BIN19 derivative).

3. Transformation of *Agrobacterium tumefaciens*

For Bin19 derivatives, the introduction of the DNA into the Agrobacteria was carried out by direct transformation using the method of Holsters et al. (Mol. Gen. Genet. (1978), 163, 181–187). The plasmid DNA transformed Agrobacteria were isolated by the method of Birnboim and Doly (Nucl. Acids. Res. (1979), 7, 1513–1523) and separated by gel electrophoresis after a suitable restriction cleavage.

4. Plant Transformation

A) Tobacco: 10 ml of an overnight culture of *Agrobacterium tumefaciens*, washed under selection, was centrifuged, the supernatant discarded and the bacteria resuspended in the same volume of antibiotic-free medium. In a sterile petri dish, leaf discs of sterile plants, (ca 1 cm$^2$), from which the middle vein had been removed, were bathed in the bacterial suspension. The leaf discs were then placed compactly in petri dishes which contained MS-medium with 2% sucrose and 0.8% bacto-agar. After two days of incubation at 25° C. in the dark they were transferred to MS-medium which contained 100 mg/l kanamycin, 500 mg/l claforan, 1 mg/l benzylaminopurine (BAP), 0.2 mg/l naphthylacetic acid (NAA) and 0,8% bactoagar. Growing shoots were put into hormone-free MS-medium with 250 mg/l claforan.

B) Potatoes: 10 small leaves of a sterile potato culture, wounded with a scalpel, were put into 10 ml MS-medium with 2% sucrose which contained 30 to 50 μl of an overnight culture of Agrobacterium tumefaciens, washed under selection. After 3–5 minutes of gentle shaking, the petri dishes were incubated at 250° C. in the dark. After two days, the leaves were placed in MSmedium with 1.6% glucose, 2 mg/l zeatinribose, 0.02 mg/l naphthylacetic acid, 0.02 mg/l gibberellic acid, 500 mg/l claforan, 50 mg/l kanamycin and 0.8% bacto-agar. After one week of incubation at 250° C. and 3000 lux, the claforan concentration in the medium was reduced by half.

C) Tomato plants: Seeds of *Lycopersicon esculentum* cv. Moneymaker were germinated in a sterile culture on MS medium supplemented with 3% sucrose (3 MS; Murashige & Skoog, 1962, Physiologia Plantarum 15:473–497). Explants from young leaves and cotyledons were sectioned in liquid 2 MS (MS medium supplemented with 2% sucrose) and preincubated for 24 to 48 hours in the dark on a *Nicotiana tabacum* W38 suspension culture feeder layer on 2 MS containing 1 mg/l NAA and 0.5 mg/l BAP. Then the explants were submerged for 5 min in a fresh overnight culture of *Agrobacterium tumefaciens* GV2260 (diluted 1:3 in 10 mM MgSO$_4$) which contained the plasmid p33-CW-INV. The explants were then dried on sterile 3MM paper and transferred back onto the feeder layer plates. After cocultivation for 48 hours in darkness the explants were washed in liquid 2 MS, dried on sterile 3MM paper and transferred to 2 MS medium containing 2 mg/l zeatin, 250 mg/l β-bactyl and 500 mg/l kanamycin for regeneration. Regenerated plantlets were transferred to soil and after acclimatization in a growth chamber, plants were cultivated in the green house.

D) Wheat: The transformation of wheat was carried out according to Becker et al.(1994, Plant J. 5:299–307).

E) Sugar beet: The transformation of sugar beet was carried out according to D'Halluin et al. (1992, BIO/TECHNOLOGY 10:309–319).

5. Analysis of the Genomic DNA from Transgenic Plants

The isolation of genomic plant DNA was carried out by the method of Rogers and Bendich (Plant Mol. Biol. (1985), 5, 69–76).

For DNA analysis, 10–20 μg of DNA was tested after suitable restriction cleavage with the aid of Southern blots to determine the integration of the DNA sequences being analyzed.

6. Analysis of the Total RNA from Transgenic Plants

The isolation of total plant RNA was carried out by the method of Longemann et al. (Analytical Biochem (1987), 163, 16–20).

For the analysis, 50 μg samples of total RNA were tested with the use of northern blots to determine the presence of the desired transcripts.

7. Protein Extraction

For the extraction of the total protein from plant tissues, tissue pieces were homogenized in protein extraction buffer (25 mM sodium phosphate pH 7.0, 2 mM sodium bisulphite, 2 mM phenylmethyl-sulphonyl fluoride (PMSF)), with the addition of 0.1% (w/v) in soluble polyvinylpyrrolidone (PVP).

After filtering through cellulose, cell particles were centrifuged off for 20 minutes at 10,000 revolutions per minute and the protein concentration of the supernatant was determined by the method of Bradford (Anal. Biochem. (1976), 72, 248–254).

8. Determination of foreign protein with the aid of immunological process (Western-Blot)

Protein extracts were separated using gel electrophoresis in SDS-PAGE (sodium dodecylsulphatepolyacrylamide) gels according to molecular weight. After SDS-PAGE, protein gels were equilibrated for 15–30 minutes in transfer buffer for graphite electrodes (48 g/l tris, 39 g/l glycine, 0.0375% SDS, 20% methanol) and then transferred into the cool room onto nitrocellulose filters and separated with 1.3 mA/cm$^2$ for 1–2 hours. The filter was saturated for 30 minutes with 3% gelatine in TBS-buffer (20 mM tris/HCl pH 7.5, 55 mM NaCl) and then the filter was incubated for 2 hours with the corresponding anti-serum at a suitable dilution (1:1000–10,000 in TBS buffer) at room temperature. The filter was then washed, each time for 15 minutes, with TBS-, TTBS- (TBS-buffer with 0.1% Tween 20) and TBS. After washing, the filter was incubated for 1 hour at room temperature with alkaline phosphatase conjugated goat-anti-rabbit (GAR)-antibodies (1:7500 in TBS). The filter was then washed as described above and equilibrated in AP-buffer (100 mM tris/HCl, pH 9.5, 100 mM NaCl, 3 mM MgCl$_2$). The alkaline phosphatase reaction was started through substrate addition of 70 μl 4-nitrotetrazolium (NBT) solution (50 mg/ml NBT in 70% dimethylformamide) and 35 μl 5-bromo-4-chloro-3-indolyl phosphate (BCIP) (50 mg/ml BCIP in dimethylformamide) in 50 ml AP buffer. After 5 minutes, the first signals could be seen. The reaction can be ended by transferring the filters to a stop solution (20 mM tris/HCl pH 8.0 with 5 mM EDTA). The reaction was carried out in darkness.

9. Identification of Invertase Activity

Acid invertase cleaves sucrose into glucose and fructose. The enzyme activity of acid invertase can be shown in plant protein extracts after separation by SDS polyacrylamide gels.

The total protein was extracted from plants as described under Paragraph 7 and treated with 2× native SB buffer (125 mM tris/HCl pH 6.8, 10% 2-mercaptoethanol, 20% glycol, 0.004% bromophenol blue) and added to 0.2% SDS gels. The extracts were not denatured by heating before separation in the SDS polyacrylamide gels. After electrophoretic separation, the gels were washed for a short time in water and incubated for 1 hour at 30° C. in sucrose solution (0.1M sucrose, 0.1M sodium acetate pH 5.0). Then the excess sucrose was removed by several washings (3×5 minutes) with water. The test for reducing sugars was carried out by boiling the gels in TPTC-reaction solution (0.1%, 2,3,5-triphenyl-tetrazolium chloride in 0.5N caustic soda) for 5–10 minutes in a microwave oven. The reaction was stopped by placing the gels in 10% acetic acid. The gels were then washed and dried. An intensive red coloration in the gel showed the presence of reducing sugars (see FIG. 7, under A, shown as black staining).

10. Isolation of vacuoles from transgenic and nontransgenic tobacco plants

Protoplasts were obtained from 3 to 4 week old sterile tobacco plants which were prepared according to known methods (Damm and Willmitzer, Mol. Gen. Genetics 217, 15–20 (1988)). Then, about 10 million protoplasts were separated from vacuoles by known methods (Boller and Kende, Plant Physiology 63, 1123–1132 (1979)). The purity of the vacuoles was confirmed microscopically and by a determination of the -mannosidase activity (Van der Wilden et al., Plant Physiology 66, 390–394 (1980)). The invertase activity determination was carried out by gel electrophoresis after the -mannosidase equalization.

In FIG. 8, it is shown that the vacuolar fraction contained comparable invertase activity to the protoplasts subjected to vacuole isolation. The results show that the sub-cellular distribution of the invertase corresponds to the vacuolar marker enzymes of the -mannosidase.

EXAMPLE 1

Preparation of plasmid p35S-Cy-INV and introduction of the plasmid into the genome of tobacco and potato plants Sucrose was split by the enzyme invertase into the two hexoses, glucose and fructose. These two hexoses are not chemically equivalent to sucrose and therefore, do not lead to a feedback of the unloading of the sucrose from the phloem. A DNA sequence from yeast that codes for the suc gene is prepared with the 35S promoter of the cauliflower mosaic virus, as well as a plant termination signal. The plant termination signal contains the 3'-end of the poly-A side of the octopine synthase gene. The plasmid p35S-Cy-INV consists of the three fragments A, B and C that are cloned into the cutting positions for restriction enzymes of the polylinker of pUC18 (see FIG. 1).

The fragment A contains the 35S promoter of the cauliflower mosaic virus (CaMV). It comprises a fragment, which includes nucleotides 6909 to 7437 of the CaMV (Franck et al, (1980) Cell 21, 285 to 294) and which was isolated as the EcoRI-KpnI fragment from the plasmid pDH51 (Pietrzak et al (1986) Nucleic Acids Res. 14, 5857–5868). Fragment A was cloned between the EcoRI-KpnI cutting sites of the plasmid pUC18.

The fragment B contains 23 nucleotides of the proteinase inhibitor II gene from the potato (*Solanum tuberosum*) (nucleotides 923–945, Keil et al (1986), Nucleic Acids Res. 14, 5641–5650) which are fused via a linker of 7 base pairs, which has the sequence AGCTTTC, to the SUC2 gene from yeast, which includes nucleotides +64 to +1765 (Taussig and Carlson (1983) Nucleic Acids Res. 11, 1943–1954).

The fragment B was inserted as an Sca/XmnI fragment between the SmaI/PstI cutting sites of the polylinker of pUC18, whereby, before the ligation, the 3'-overhanging ends of the PstI cutting site was rendered blunt through incubation with a T4-DNA polymerase.

The fragment C contains the polyadenylation signal of the gene 3 of the T-DNA of the Ti-plasmid pTiACH5 (Gielen et al (1984); EMBO J. 3, 835–846), and nucleotides 11749–11939, which were isolated as the PvuII-HindIII fragment from the plasmid pAGV 40 (HerreraEstrella et al (1983) Nature 303, 209–213). Fragment C was cloned, after addition of SphI-linker, into the PvuII cutting site between the SphI-HindIII cutting site of the polylinker of pUC18. The plasmid p35S-Cy-INV has a size of 5.1 kb (see FIG. 1). The part of the plasmid p35S-Cy-INV containing the fragments A, B and C, was introduced into binary vectors. Then the Agrobacterium system was used to introduce the vectors into tobacco and plant cells. From the transformed cells, intact and fertile plants were regenerated. The analysis of the regenerated plants showed that in all analyzed tissues (leaf and stem) there was an invertase activity that was not found in the non-transformed plants. Through immunological processes, it was shown that this invertase is a yeast invertase. This invertase is localized in the cytosol and/or cytoplasm. Therefore, it was shown that the expression cassette which included a yeast invertase gene was able to produce transgenic tobacco and potato plants that contained a new invertase activity in all organs and cells. The regenerated tobacco and potato plants were clearly distinguishable from the nontransformed plants. The leaves showed a variation in green color. Further, individual transformed plants variously showed strong growth intensity which led to a shortening of the internode distance in the same leaf. Further, it could be observed that the young leaves turned slightly inwards.

EXAMPLE 2

Preparation of the plasmid p35S-CW-INV and introduction of the plasmid into the genome of tobacco and potato plants In a similar process as that described under Example 1, the plasmid p35S-CW-INV was prepared with the modification that a signal peptide necessary for the uptake of the plant gene in the endoplasmic reticulum (proteinase inhibitor II gene from potato (*Solanum tuberosum*), Keil et al 1986) was introduced before the coding sequence of the invertase gene. The plasmid p35S-CW-INV had a size of 7.1 kb and consisted of the three fragments A, B and C which were cloned in the given cutting sites for restriction enzymes of the polylinker of pMPK110 (see FIG. 2).

The fragment A consists of the 35S promoter of the cauliflower mosaic virus (CaMV). It contains a fragment, which includes nucleotides 6909 to 7437 of the CaMV (Franck et al (1980) Cell 21, 285–294) and which was isolated as the EcoRI-KpnI fragment from the plasmid pDH51 (Pietrzak et al (1986) Nucleic Acids Res 14, 5857–5868) and which was cloned between the EcoRI-KpnI cutting sites of the plasmid pMPK110.

The fragment B contains nucleotides 923–1159 of a proteinase inhibitor II gene of the potato (*Solanum tuberosum*) (Keil et al (1986) Nucleic Acid Res 14, 5641–5650) which are fused via a linker, with the sequence ACC GAA TTG GGG ATC CCA GCT TTC (SEQ ID No. 1), to the SUC2 gene from yeast, which includes nucleotides +64 to +1765 (Taussig and Carlson (1983) Nucleic Acid Res 11, 1943–1954). Fragment B also includes a plant protein N-terminal signal peptide which is necessary for the uptake of proteins into the endoplasmic reticulum and which is fused to the invertase sequence. Fragment B was introduced as a Sca/XmnI fragment, between the SmaI/PstI positions of the polylinker of pMPK110, whereby before the ligation, the 3' overhanging ends of the PstI cutting sites were rendered blunt by incubation with a T4 DNA polymerase.

The fragment C contains the polyadenylation signal of the gene 3 of the T-DNA of the Ti-plasmid pTiACH5 (Gielen et al (1984) EMBO J. 3, 835–846, nucleotides 11748–11939) which was isolated as a PvuII-HindIII fragment from the plasmid PAGV 40 (HerreraEstrella et al (1983) Nature 303, 209–213) and which was cloned, after addition of SphI-linker at the PvuII cutting sites, between the SphI-HindIII cutting sites of the polylinker of pMPK110 (see FIG. 2).

The part of the plasmid p35S-CW-INV which contains the fragments A, B and C was introduced into the plants in an analogous way to that described in Example 1. The analysis of the transgenic plant by means of Western-blot and activity tests showed that the invertase coded from the SUC2 gene is now localized in the extracellular space. Transgenic tobacco and potato plants that contain this chimeric gene show, in addition to a shortening of the plants based on the reduced internode distance, a new leaf phenotype that extends from the formation of a mosaic pattern, to green and chlorotic areas which stretch up to the formation of necrotic areas. Further, the transgenic plants showed highly reduced root formation.

EXAMPLE 3

Preparation of the plasmid p33-CW-INV and introduction of the plasmid in the potato plant genome The plasmid p33-CW-INV was prepared in a similar manner to that described in Example 2, except that the 35S promoter was replaced by the promoter of the class I patatin gene B33 (Rocha-Sosa et al (1989) EMBO J 8, 23–29). The plasmid p33S-CW-INV had a size of 7.0 kb and comprised the three fragments A, B and C which were cloned in the cutting sites for restriction enzymes of the polylinker of pUC118 (see FIG. 3).

The fragment A contains the DraI-DraI fragment (position −1512 to position +14) of the promoter region of the patatin gene B33 (Rocha-Sosa et al (1989) EMBO J. 8, 23–29) which was cloned in the SmaI position of the polylinker of pUC118.

The fragments B and C correspond to the fragments B and C in the plasmid p35S-CW-INV (see FIG. 2). For cloning of the fragments B and C, the plasmid p35S-CW-INV was digested with Asp718 (partial) and HindIII. The resulting ends of the HindIII cutting sites were completed with DNA polymerase (Klenow fragment). Then the fragments which contained both intact fragments B and C were separated, by means of gel-electrophoresis, from other fragments. The fragment which contained the B and C fragments was then cloned in the above orientation between the EcoRI cutting site filled with DNA polymerase (Klenow fragment) and partially with G+A, and the Asp718 cutting site. By partial filling, the HindIII cutting site was obtained.

The plasmid p33-CW-INV was introduced into the plant in a similar manner as described in Example 1. In the potato, the chimeric gene leads to a tuber specific expression of the invertase.

Two transgenic potato plants of the species, Desiree, which had been transformed with the plasmid p33-CW-INV, were fully compared under growth conditions, in relation to habit and yield, with control plants which had not been transformed. It was surprisingly found that the most significant difference between the transformed plants and the untransformed plants was in the tuber yield. The two plants, transformed with the plasmid p33-CW-INV, which were grown under greenhouse conditions, showed a potato yield of 283 and 223 g respectively, whereas both control plants only showed a tuber yield of 155 and 132 g of fresh weight, respectively. The determination of the dry weight as well as the total starch content of the potatoes showed the same relative uptake in the plants transformed with the plasmid p33-CW-INV as compared to the control plants. This means that the introduction and the tuber specific expression of the plasmid p33-CW-INV in transgenic potato plants has increased the yield of these plants by around 50 to 100% (see FIG. 8). In relation to the size distribution of the tubers, the plants transformed with the plasmid p33-CW-INV yielded significantly more large tubers (see FIG. 8). This means that the introduction and expression of the plasmid p33-CW-INV leads not only to a significant increase of the total potato tuber yield in potato plants, but also to an increase in the size of the individual potato tubers.

EXAMPLE 4

Preparation of the plasmid D1700-CW-INV and introduction of the plasmid into the genome of tobacco and potato plants In a similar manner to that described in Example 2, the plasmid p1700-CW-INV was prepared, except that the 35S promoter with the leaf specific promoter of the ST-LS1 gene (Stockhaus et al (1987) Proc. Natl. Sci. USA 84, 7943–7947).

The plasmid p1700-CW-INV had a size of 8.4 kb and consisted of the three fragments A, B and C that were cloned into restriction sites within the polylinker of pMPK110 (see FIG. 4).

The fragment A contained the EcoRI-MboII fragment of the ST-LS1 potato gene. The position of the MboII side in relation to the published sequence (Eckes et al (1986) Mol Gen Genetics 205, 14–22) lies at position 1585 (position +1 to position +1585). This fragment was cloned between the EcoRI-SmaI cutting site of the polylinker of pUC18, in which the overhanging 3' end of the MboII cutting site had been previously rendered blunt by T4-DNA polymerase.

The fragments B and C correspond to the fragments B and C in plasmid p35S-CW-INV (see FIG. 2). For cloning fragments B and C, the plasmid p35S-CW-INV was partially digested with Asp718. The resulting 3' ends were completed with DNA polymerase (Klenow fragment) and the plasmid was then cleaved with HindIII. The intact fragments B and C were then separated from other fragments by gel electrophoresis. The desired fragments were then purified and cloned between the BamHI-HindIII cutting sites of the polylinker of pMPK110. The BamHI cutting site had previously been rendered blunt by filling with DNA polymerase I.

The part of the plasmid p1700-CW-INV, containing fragments A, B and C was introduced into plants in a similar manner to that described in Example 1.

EXAMPLE 5
Preparation of the plasmid p33-Cy-INV and introduction of plasmids in the genome of tobacco and potato plants The plasmid p33-Cy-INV was prepared in a similar manner to that described in Example 1, except that the 35S promoter was replaced with the promoter of the Class I patatin gene B33 (Rocha-Sosa et al (1989) EMBO J 8, 23–29).

The plasmid p33-Cy-INV had a size of 6.8 kb and consisted of three fragments A, B and C which were cloned into the restriction enzyme cutting sites of the polylinker of pUC118 (see FIG. 5).

The fragment A contained the DraI-DraI fragment (site −1512 to position +14) of the promoter region of the patatin gene B33 (Rocha-Sosa et al (1989) EMBO J. 8, 13–29) which was cloned in the SmaI position of the polylinker of pUC118.

The fragments B and C correspond to the fragments B and C in plasmid p35S-Cy-INV. For cloning the fragments B and C, the plasmid p35S-Cy-INV was digested with HindIII, the resulting 3' end being completed with DNA polymerase (Klenow Fragment). The plasmid was partially digested with Asp 718 and both intact fragments B and C were separated by gel electrophoresis from other fragments. These fragments were then cloned between the Asp718 and the EcoRI cutting sites of the polylinker of pUC118 which is filled with DNA polymerase, partially with G+A. By the partial filling, the HindIII cutting sites were obtained.

The plasmid p33-Cy-INV was introduced into the plants in a similar manner as described in Example 1.

EXAMPLE 6
Preparation of the plasmid p34S-V-INV and introduction of the plasmid in the genome of tobacco plants In a similar manner to that described in Example 1, the plasmid p35S-V-INV was prepared, with the modification that, in front of the coding sequence of the invertase gene, a peptide of a plant gene (patatin-gene pgT5 from potato, Rosahl et al., Mol. General Genetics 203, 214–220), which is necessary for the direction of the invertase protein into the vacuole, was fused. The plasmid p35S-V-INV had a size of 6.3 kb and consisted of the three fragments A, B and C, which were cloned into the given cutting sites of the polylinker of pUC 18 (see FIG. 6). Fragment A (529 bp) contains the 35S promoter of the cauliflower mosaic virus (CaMV), including nucleotides 6909 to 7437 of the CaMV (Franck et al., Cell 21, 285–294). Fragment A was isolated as the EcoRI-KpnI fragment from the plasmid pDH51 (Pietrzak et al., Nucleic Acid Research 14, 5857–5868) and was cloned between the EcoRI-KpnI cutting sites of the polylinker of the plasmid pUC18 (see FIG. 6).

Fragment B contains nucleotides +707 to +1895 of the sequence of the genomic patatin clone pgT5 (Rosahl et al., 1986) which are fused via a linker, with the sequence AGCTTTC, to the SUC2 gene from yeast, which includes nucleotides +64 to +1765 (Taussig and Carlson, (1983) Nucleic Acid Res. 11, 1943–1954). In this way, a peptide responsible for the direction of proteins into the vacuoles of higher plants and which has a corresponding vacuolar N-terminal targeting signal is fused to the invertase sequence. The fragment B was introduced as an EcoRV-XmnI fragment between the SmaI/PstI cutting sites of the polylinker of pUC18 (see FIG. 6). Prior to the ligation, the 3'-overhanging ends of the PstI cutting site were rendered blunt by incubation with a T4-DNA-polymerase.

Fragment C (192 bp) includes the polyadenylation signal of the T-DNA gene 3 of the Ti-plasmid pTiACH5 (Gielen et al, EMBO J. 3, 835–846) with nucleotides 11749–11939, which was isolated as the PvuII-HindIII fragment from the plasmid pAGV40 (HerreraEstrella et al (1983) Nature 303, 209–213). After the addition of the SphI linkers, the fragment was cloned to the PvuII cutting sites between the SphI-HindIII cutting sites of the polylinker of pUC18.

Analysis of the resulting transgenic tobacco plant by means of invertase activity tests showed that the invertase coded from the SUC2 gene is now localized in the vacuole (see FIG. 9). Transgenic tobacco plants showed, in addition to a shortening of the plants, a new leaf phenotype. The new leaf phenotype is characterized in that chlorotic areas beginning at the leaf tips developed in older leaves.

EXAMPLE 7
Preparation of the plasmid pUSP-CW-INV and introduction of the plasmid into the plant genome of tobacco and wheat plants For the preparation of the plasmid pUSP-CW-INV, a DNA fragment comprising the seed specific promoter and the nontranslated leader sequence of the USP gene of *Vicia faber* was isolated as a PstI fragment of approximately 688 bp from the plasmid pP30T, a derivative of pP30 (Fiedler et al., 1993, Plant Mol. Biol. 22:669–697). This fragment comprises nucleotides −637 to +51 of the USP gene as published by Baumlein et al. (1991, Mol. Gen. Genet. 225:459–467) and is flanked on its 5' side by a PstI restriction site and on its 3' side by a linker sequence containing restrictions sites for BglII, SphI and PstI. The PstI fragment was ligated into a pBluescriptKS+ vector (Stratagene) linearised with PstI. From the analyzed recombinant clones, a clone was chosen in which the PstI fragment was ligated into the vector so that the BglII site of the downstream linker sequence of the fragment was next to the BamHI site of the polylinker of the pBluescript vector. The resulting plasmid was named pBS-USP.

From this plasmid the fragment containing the promoter and the 5' nontranslated leader was isolated as a XbaI/EcoRI fragment of approximately 700 bp. This fragment was ligated into the vector pBinAR-Hyg (DSM 9505) which had been cut with the restriction enzymes XbaI and EcoRI. The resulting plasmid, pBIN-USP-Hyg, is shown in FIG. 10. It comprises the following DNA fragments:

Fragment A contains the promoter and the nontranslated leader sequence of the USP gene of *Vicia faber*. It includes nucleotides −637 to +51 of the USP gene (Bäumlein et al., 1991, Mol. Gen. Genet. 225:459–467), a polylinker with various restriction sites and Fragment C contains the polyadenylation signal of the gene 3 of the T-DNA of the Ti-Plasmid pTiACH5 (Gielen et al., 1984, EMBO J. 3:835–846). It comprises nucleotides 11749–11939 of the cauliflower mosaic virus.

In order to prepare a binary vector suitable for the transformation of plant cells and for the selection of kanamycin resistance of transformed cells, an EcoRI/HindIII fragment of approximately 900 bp was isolated from pBIN-USP-Hyg. This fragment comprises fragment A, the polylinker and fragment C of pBIN-USP-Hyg. It was ligated into the binary vector pBIN19 (Bevan et al., 1984, Nucl. Acids Res. 12:8711–8721; commercially available from Clontech Laboratories, Inc., USA), which had been cut with EcoRI and HindIII. The resulting vector pUSP-Bin19 was used to prepare an expression cassette for the seed specific expression of an invertase.

For this purpose, a DNA fragment corresponding to the fragments B and C of the plasmid p35S-CW-INV, as described in Example 2, was isolated. This DNA fragment was isolated as an EcoRI/HindIII fragment of approximately 2000 bp from a suitable plasmid in which this fragment was flanked by an EcoRI restriction site on the 5' site and a HindIII restriction site on the 3' site. The EcoRI site was filled in order to create a blunt end. This fragment was then ligated into the vector pUSP-Bin19 which had been previously cut with SmaI and HindIII. The resulting plasmid pUSP-CW-INV is shown in FIG. 11 and consists of the following DNA fragments:

Fragment A contains the promoter and the 5' nontranslated leader sequence of the USP gene of *Vicia faber*. It comprises a fragment which includes nucleotides −637 to +51 of the USP gene (Bäumlein et al., 1991, Mol. Gen. Genet. 225:459–467).

Fragment B contains nucleotides +923 to +1159 of a proteinase inhibitor II gene of *Solanum tuberosum* (Keil et al., 1986, Nucl. Acids Res. 14:5641–5650) fused to the SUC2 gene of yeast (nucleotides +64 to 1765; Taussig and Carlson, 1983, Nucl. Acids Res. 11:1943–1954) via a linker sequence with the sequence ACC GAA TTG GGG ATC CCA GCT TTC (SEQ ID No. 1).

Fragment C contains the polyadenylation site of the gene 3 of the T-DNA of the Ti-plasmid pTiACH5.

The plasmid pUSP-CW-INV has a length of approximately 13 kb.

This plasmid was introduced into tobacco plants using the Agrobacterium system, as described above, and into wheat plants using particle bombardment, as described above. From the transformed cells, intact and fertile plants were regenerated and analyzed for invertase activity in various tissues.

EXAMPLE 8

Expression of an apoplastic invertase in tomato fruits

For the expression of an apoplastic invertase in fruits of tomato plants, the plasmid p33-CW-INV was introduced into tomato plants as described above. Transgenic plants were tested for invertase activity in fruit tissue. Two of the transgenic lines tested showed strong invertase activity in tomato fruits.

EXAMPLE 9

Expression of an apoplastic invertase in tap roots of sugar beet plants

For the expression of an apoplastic invertase in the tap roots of sugar beet plants, the plasmid p33-CW-INV was transferred into cells of sugar beet plants, as described above. Then intact plants were regenerated from the transformed cells. The transformed plants were analyzed for invertase activity in the tissues of the tap root.

Although the present invention has been described in relation to particular embodiments thereof, many other variations and modifications and other uses will become apparent to those skilled in the art.

What is claimed is:

1. A plant containing a plasmid which comprises a plant species specific patatin promoter operably linked to a DNA sequence encoding a polypeptide which comprises a signal peptide fused to invertase wherein the signal peptide is functionally capable of directing the translocation of the invertase to a desired location in a plant cell.

2. A plant according to claim 1, wherein said desired location is a plant cell apoplast.

3. A plant according to claim 2, wherein the plant is a crop plant.

4. A plant according to claim 3, wherein the crop plant is selected from the group consisting of tobacco, potato, tomato, sugar beet, soya bean, wheat, barley, corn, oat, rice and sugar cane plants.

5. A plant according to claim 2, wherein said plasmid is p33-CW-INV deposited as DSM 5787.

6. A plant according to claim 5, wherein the plant is a crop plant.

7. A plant according to claim 6, wherein the crop plant is selected from the group consisting of tobacco, potato, tomato, sugar beet, soya bean, wheat, barley, corn, oat, rice and sugar cane plants.

8. A plant according to claim 1, wherein the plant is a monocot.

9. A plant according to claim 1, wherein the plant is a dicot.

10. A plant according to claim 1, wherein said desired location is a plant cell vacuole.

11. A plant according to claim 10, wherein the plant is a crop plant.

12. A plant according to claim 11, wherein the crop plant is selected from the group consisting of tobacco, potato, tomato, sugar beet, soya bean, wheat, barley, corn, oat, rice and sugar cane plants.

13. A plant according to claim 11, wherein said plasmid is p33-CW-INV deposited as DSM 5787.

14. A method for the preparation of a plant with an increased dry weight of a sink organ comprising transforming plants with plasmid p33-CW-INV deposited as DSM 5787.

15. The method according to claim 14, wherein the sink organ is selected from the group consisting of seeds, fruits, roots and tubers.

16. A plasmid containing a DNA sequence, wherein the DNA sequence directs the translocation of invertase to a vacuole of a plant cell, said DNA sequence is operably linked to a DNA sequence encoding invertase, wherein the DNA sequence directing the translocation of invertase to a vacuole of a plant cell comprises nucleotide position +707 to +1895 of patatin gene pgT5 from *Solanum tuberosum* (SEQ. ID No. 2) or sequences which hybridize to the DNA sequence directing the translocation under stringent conditions.

17. Plasmid p35S-V-INV deposited as DSM 6142.

18. A plant stably transformed with a plasmid according to claim 17.

19. A plant according to claim 18, wherein the plant is a crop plant.

20. A plant according to claim 19, wherein the crop plant is selected from the group consisting of tobacco, potato, tomato, sugar beet, soya bean, wheat, barley, corn, oat, rice and sugar cane plants.

21. A plant cell transformed with a plasmid which comprises a plant species specific patatin promoter operably linked to a DNA sequence encoding a polypeptide which comprises a signal peptide fused to invertase wherein the signal peptide is functionally capable of directing the translocation of the invertase to a desired location in a plant cell.

22. A plant cell according to claim 21, wherein said desired location is a plant cell apoplast.

23. A plant cell according to claim 22, wherein the plant cell is obtained from a crop plant.

24. A plant cell according to claim 22, wherein the plant cell is obtained from a monocot.

25. A plant cell according to claim 22, wherein the plant cell is obtained from a dicot.

26. A plant cell according to claim 22, wherein said plasmid is p33-CW-INV deposited as DSM 5787.

27. A plant cell according to claim 21, wherein said desired location is a plant cell vacuole.

28. A plant cell according to claim 27, wherein said plasmid is p33-CW-INV deposited as DSM 5787.

29. A plant cell according to claim 27, wherein the plant cell is obtained from a crop plant.

30. A plant cell according to claim 27, wherein the plant cell is obtained from a monocot.

31. A plant cell according to claim 27, wherein the plant cell is obtained from a dicot.

32. A method for the production of transgenic plants, comprising the following steps:

a) producing an expression cassette having the following sequences:
      i) a class I patatin promoter, operably linked to,
      ii) a DNA sequence encoding invertase, fused to
      iii) a DNA sequence of a signal peptide, wherein the signal peptide is functionally capable of directing the translocation of the invertase to a desired location in a plant cell;

b) transferring the expression cassette into plant cells, thereby producing transformed plant cells; and c) regenerating whole, intact transgenic plants from the transformed cells.

33. A method according to claim 32, wherein said desired location is a plant cell vacuole.

34. A method according to claim 33, wherein said plants are monocots.

35. A method according to claim 33, wherein said plants are dicots.

36. A method according to claim 32, wherein said desired location is a plant cell apoplast.

37. A method according to claim 36, wherein said plants are monocots.

38. A method according to claim 36, wherein said plants are dicots.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ACCGAATTGG GGATCCCAGC TTTC            24

(2) INFORMATION FOR SEQ ID NO:2:

(i) SEQUENCE CHARACTERISTICS:
      (A) LENGTH: 1189 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Solanum tuberosum
        (C) INDIVIDUAL ISOLATE: patatin gene (vii) IMMEDIATE SOURCE:
        (A) LIBRARY: genomic clone pgT5

(xi) SEQUENCE DESCRIPTION: SEQ ID NO:2:

```
ATCAGTTTTT ATTAATTATA ATCTGCAAAA TGGCAACTAC TAATTCTTTT ACAATTTTAA        60

TTTTTATGAT ATTAGCAACT ACTAGTTCAA CATTTGCTAC GTTGGGAGAA ATGGTGACTG       120

TTCTTAGTAT TGATGGAGGT GGAATTAAGG GAATCATTCC GGCTACCATT CTCGAATTTC       180

TTGAAGGACA ACTTCAGGTA TCGTAAAAAT ATTTTGTAAT GTATGTACGT AAGTGTGACA       240

CTACTATAGT CATTCCAGGT ACCATTCTTG ATTTTCTTGA AGGACAACTT CAGATATCGT       300

AAAAACATTT TTTTGTGTAT GTATGTAAGT GTGACATTAC AATCGTTTTT TTCTTTTTTT       360

ACACTTGAAT TGTTTTTTTT CGATGCTTAT TAATGATAAT GATTAGTAAT AGTACCTCTA       420

TTATCGATAT GGTCATGATA AAGCTAATTA TTATTCAAAT AAATAATGGT TTTCTTATGT       480

TACAACTTAT TTACTAATTT TTTTAATATA TAAATGTACT GTCTAATTAA TAAGTGAGTT       540

ATTTTTGAGT TATTATTTAT ACGACTTATT TTTCTTTTCG AGTCAGGAAG TGGACAATAA       600

TACAGATGCA AGACTTGCAG ATTACTTTGA TGTAATTGGA GGAACAAGTA CAGGAGGTTT       660

ATTGACTGCT ATGATAACTA CTCCAAATGA AACCAATCGA CCATTTGCTG CTGCCAAAGA       720

TATTGTACCT TTTTACTTCG AACATGGCCC TAAGATTTTT CAATCTAGGT ACATATACAT       780

ATTTATATTT GTTTATTTTA ATTTATTTGT CTAATTTTAA CTTGATATGA AGTTTAAGAG       840

CGTGAAAAAA GATTTTTGAA TCTTCTAGTT TTAAATTGAT GAAATGTCAA ATGTATCAAA       900

ATATCATCAG ATACATCCCT CCCATTAATT AATGCATCAT TTGCAATGTA TCGGACAACC       960

AAGGAAAATA TCCGAGAGCA ATGAAATATT TAGTAGTTTT ATACGTAATT GAGTAAACTT      1020

CTAAGACAGG ATATAATCAA CCCCAAATAT ATGAGATTTA TGTTCTTTAT ACTTATATTT      1080

AATTTGGTTA CATTATATTA TGCAGTGGTT CAATTTTTGG CCCAAAATAT GATGGAAAAT      1140

ATCTTATGCA AGTTCTTCAA GAAAAACTTG GAGAAACTCG TGTGCATCA                 1189
```